United States Patent [19]

Ortiz et al.

[11] Patent Number: 4,974,456
[45] Date of Patent: * Dec. 4, 1990

[54] ZERO HEAD SPACE SAMPLING METHOD

[75] Inventors: Patricia A. Ortiz, Angleton; Stanley J. Reynolds, Jr.; Daniel E. Moss, both of Lake Jackson, all of Tex.

[73] Assignee: The Dow Chemical Company, Midland, Mich.

[*] Notice: The portion of the term of this patent subsequent to Sep. 12, 2006 has been disclaimed.

[21] Appl. No.: 368,625

[22] Filed: Jun. 20, 1989

Related U.S. Application Data

[62] Division of Ser. No. 160,553, Feb. 24, 1988, Pat. No. 4,864,877.

[51] Int. Cl.$^5$ .............................................. G01N 1/20
[52] U.S. Cl. .............................. 73/863.52; 73/863.71; 141/59; 222/478
[58] Field of Search ............ 73/863.01, 863.31, 863.33, 73/863.52, 863.58, 863.61, 863.71, 863.86, 864, 864.51, 864.63, 864.91, 863.41; 141/324, 311 R, 35, 59, 7; 220/303, 288; 215/276; 222/478, 479

[56] References Cited

U.S. PATENT DOCUMENTS

| | | | |
|---|---|---|---|
| 643,605 | 2/1900 | Pendergraft | 141/59 |
| 1,403,636 | 1/1922 | Rhodes | 222/478 |
| 2,294,655 | 9/1942 | Einstein | 73/864.634 X |
| 2,300,194 | 10/1942 | Anderson | 73/864.634 X |
| 2,840,123 | 6/1958 | Metcalfe | 141/7 X |
| 2,884,021 | 4/1959 | Ginsburg | 141/35 |
| 3,811,484 | 5/1974 | Engelbrecht | 141/35 X |
| 3,842,677 | 10/1974 | Bufkin et al. | 73/863.31 |
| 4,454,772 | 6/1984 | Brunner et al. | 73/863.31 |
| 4,596,156 | 6/1986 | Shimizu et al. | 73/863.31 |
| 4,773,252 | 9/1988 | Jarolics | 73/863.31 X |
| 4,817,445 | 4/1989 | Fink | 73/864.63 X |
| 4,818,489 | 4/1989 | Gönner et al. | 73/864.51 X |
| 4,864,877 | 9/1989 | Ortiz et al. | 73/863.31 X |

FOREIGN PATENT DOCUMENTS 966441 9/1955 France .............................. 222/478

OTHER PUBLICATIONS

"An Automated Multisampler-Stream Chemical Monitoring System", *American Loboratory*; vol. 9, No. 2, pp. 47-48, 50, 252; Feb. 1977; Heinz P. Kollig.

*Primary Examiner*—Tom Noland
*Attorney, Agent, or Firm*—W. J. Lee

[57] ABSTRACT

A sampling apparatus is disclosed including a sample container with a removable cap; an inlet conduit adapted for introducing a stream of fluid into the sample container; an outlet conduit adapted for removing a stream of fluid from the sample container; a valve in the inlet conduit for passing a stream therethrough and into the sample container; a valve in the outlet conduit for passing a stream therethrough and out of the sample container; and a controller for actuating the valve in the inlet and outlet conduits at a predetermined time interval such that a stream of fluid is passed into the sample container until the container is filled with the fluid. A method of collecting samples with a zero headspace in the collection sample container is also disclosed utilizing the above sampling apparatus.

4 Claims, 3 Drawing Sheets

ZERO HEAD SPACE SAMPLING METHOD

This is a divisional of application Ser. No. 160,553 filed Feb. 24, 1988, now U.S. Pat. No. 4,864,877.

BACKGROUND OF THE INVENTION

This invention relates to a sampling system and method and more particularly, this invention relates to an automatic sampling system and method which is advantageously used in collecting samples in sample containers with a substantially zero head space.

It is known to use sampling apparatuses in applications such as waste treatment, stream monitoring, pollution abatement, industrial effluent control, water management studies, and environmental law enforcement. Waste water streams, for example, have to be checked periodically to see if the streams meet with current standards for clean water controls and therefore sampling of the streams must be obtained to analyze such sample in order to check that the streams are in compliance with the regulations regarding the environment.

For example, in sampling waste water streams, the Environmental Protection Agency (EPA) requires that at volume of sample of a waste water stream be collected at four evenly spaced intervals over a twenty-four hour period (every/six hours). Each of the four sample volumes must be collected in individual containers and all headspace (air gap) in the containers must be eliminated. Elimination of air gap from the container is important because air in the sample container can cause inaccurate analysis of the components of interest in the collected sample. This sampling required by the EPA is usually done manually by grab samples. However, with grab sampling uniform sampling is usually not carried out because sampling techniques of individuals can vary from individual to individual. Usually an air space is collected in the sample container using manual grab samples.

An alternative to grab samples is an automatic sampling system. An automatic sampling system would save an operator's time and cost in obtaining the required samples, particularly when samples are required at, for example, six hour intervals every twenty-four hours.

There are known automatic liquid samplers which use positive sample recovery. However, a positive sample recovery type automatic liquid sampler does not adequately eliminate all of the head space in a sample collection container during operation. Therefore, such sampler would not satisfactorily comply with the EPA's requirements of collecting samples as discussed above.

It would be desirous to provide an automatic sampling system and procedure to collect samples in containers with a zero headspace.

SUMMARY OF THE INVENTION

One aspect of the present invention is directed to a sampling apparatus comprising:

(a) a sample container with a removable cap;

(b) an inlet conduit adapted for introducing a stream of fluid into said sample container;

(c) an outlet conduit adapted for removing a stream of fluid from said sample container;

(d) a valve in said inlet conduit for passing a stream therethrough and into the sample container;

(e) a valve in said outlet conduit for passing a stream therethrough and out of the sample container; and (f) a controller for actuating the valve in said inlet and outlet conduit at a predetermined time interval such that a stream of fluid is passed into the sample container until the container is filled with the fluid.

Another aspect of the present invention is directed at a method of collecting samples of fluid in a container with zero head space comprising activating valve means such that a fluid stream is flowed into a sample container near the bottom of the container and exits the container near the top of the container sufficient to purge the head space in the container.

DETAILED DESCRIPTION OF THE PREFERRED EMBODIMENTS

Figure 1:
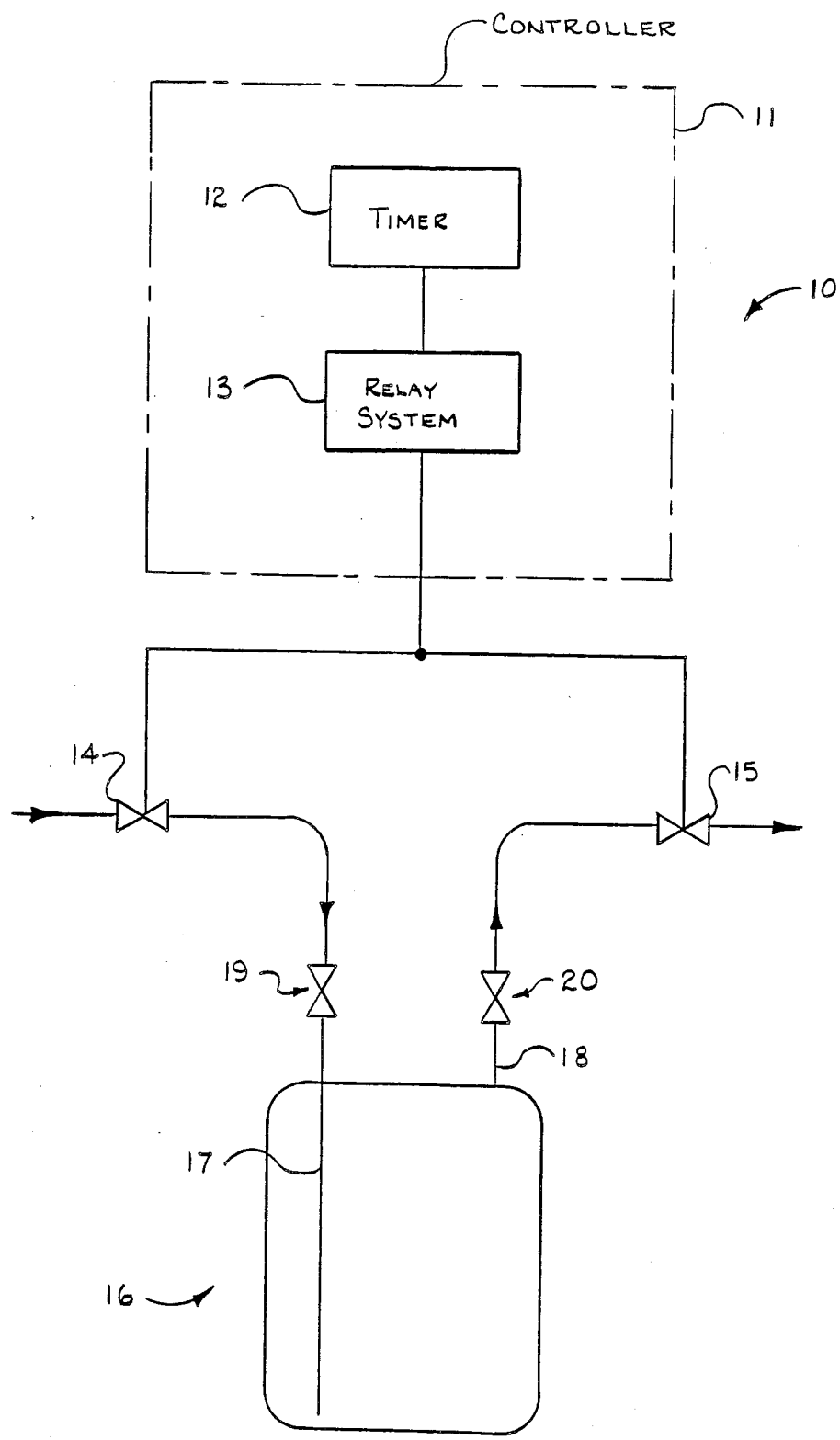
FIG. 1 is a schematic view showing the sampling system of the present invention.

With reference to FIG. 1, there is shown a sampling system of the present invention, generally designated as numeral 10, which includes a controller 11 which may comprise, for example, a timer 12 and a relay system 13.

It is understood that the controller 11 can be a microprocessor or other conventional type of controlling means. In this instance, using a timer 12 and relay system 13, a sample cycle is initiated at a time interval determined by the timer 12 which then activates the relay 13. The relay 13 energizes (opens) an inlet valve 14 and an outlet valve 15 allowing sample fluid to flow to and fill a sample container, generally designated as numeral 16, and described in more detail with reference to FIG. 2. The flow of fluid through the sampling system may be under, pressure or carried out by any conventional pumping means.

The valves 14 and 15 may be any conventional solenoid valve. The sample container 16 is filled with fluid through an inlet conduit or tube 17 and the sample fluid overflows out through an outlet conduit or tube 18 eliminating any headspace or air gap in the container 16. At a programmed interval, the timer 12 de-energizes (closes) the solenoid valves 14 and 15, respectively, which stops the sample flow to the container 16 and seals the sample container 16 ending the sample cycle. The sample container 16 filled with fluid is then removed by disconnecting a pair of valves or fittings, generally indicated by numerals 19 and 20, on the inlet tube 17 and outlet tube 18, respectively, of the sample container 16.

Figure 2:
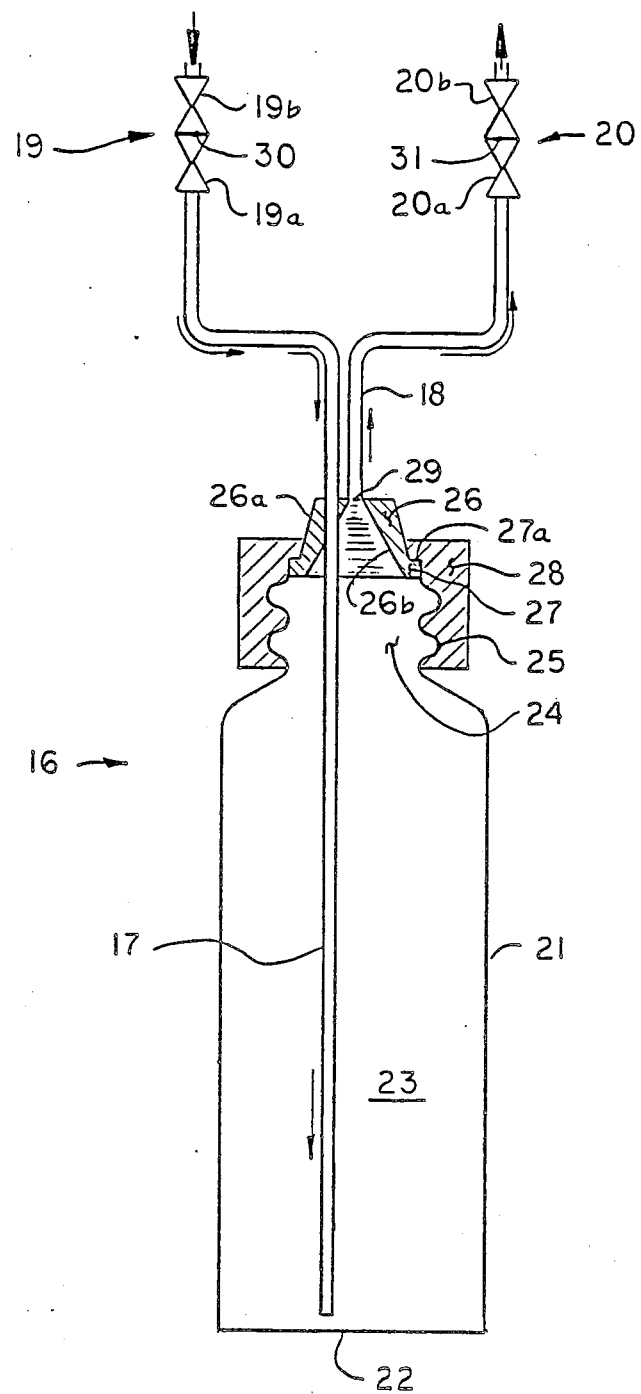
FIG. 2 is a cross-section view of a sample container of the present invention.

Referring to FIG. 2, there is shown in more detail the sample container 16 with inlet and outlet tubes 17 and 18 and fittings 19 and 20, respectively. The sample container 16, in this instance, comprises a tubular or cylindrical in shape body portion 21 with a closed end 22 forming a fluid chamber 23 and an open end tubular neck portion 24 of a smaller diameter than the body portion 21 integral with the body portion 21 which is threaded 25 and adapted to receive a removable closure cap means 26.

The cap means 26 is disposed on the top of the neck portion 24. The removable cap means 26 contains an outside surface 26a and an inside surface 26b. The inside surface 26b of the cap means is tapered such that it is generally conical in shape when viewed in cross-section. The outside surface 26a is generally frustoconical in shape when viewed in cross-section. The cap means 26 includes a flange portion 27 with a shoulder 27a adapted for receiving a threaded closure ring member 28 for securing the cap means 26 to the top of the neck portion 24 of the container 16.

The inlet tube member 17 passes through the cap means 26 into the chamber 23 to near the bottom of the container 16. The outlet tube member 18 is integral with a bore 29 at the apex of the cone of the inside surface of the cap means 26. When the sample container 16 fills, the fluid in the container overflows out through the cone-shaped inside surface of the cap means and through the outlet tube 18, and, thus, any headspace or air gap in the container chamber is eliminated by the flow of fluid pushing the air gap out through the bore 29 and through the outlet tube member 18.

The fittings 19 and 20 may be any means for shutting flow of fluid to and from the sample container 16 and detachably removing the sample container 16 from the inlet and outlet conduits 17 and 18 respectively. For example, fitting 19 can comprise two valve means 19a and 19b and fitting 20 can comprise two valve means 20a and 20b. Once the container 16 is filled with fluid the valves 19a, 19b, 20a and 20b can be closed in a fluid-tight manner and detached at point 30 and 31 such that valves 19a and 20a remain with the sample container 16. Valves 19a and 20a together with container 16 are removed and taken to a laboratory or use point for analysis.

The fittings 19 and 20 are preferably quick-connect types which comprise two sections coupled together with each section containing a shut-off valve. The quick-connect fittings can be coupled and uncoupled by a pushing and/or pulling action. The fittings separate at points 30 and 31 into two sections indicated by numerals 19a, 19b, 20a and 20b. One section, 19b and 20b of each of the fitting 19 and 20, respectively, after disengagement remains on the inlet tube 17 and outlet tube 18, respectively, of the sample lines containing valves 14 and 15 of the sampler which blocks any sample flow to the container 16. The other section 19a and 20a of each of the fitting, after disengagement, remains on the inlet tube 17 and outlet tube 18 connected to the sample container 16 which seals in the contents of the container 16 while the container is transported to a laboratory for analysis. This procedure eliminates the possibility of any head space developing in the sample container due to evaporation or spillage of the sample. Exemplary of the above quick-connect fittings 19 and 20 are commercially available SWAGELOK instrumentation quick-connect fittings which are commercially available from Cole-Parmer Instrument Company, Chicago, Ill.

The container and tube members can be made of any material which will not adversely effect the samples and the analysis of the components of interest in the samples. For example, in collecting waste water sample, the container is made of glass and the tubing members are made of TEFLON (trademark of E. I. duPont DeNemours and Company). The size of the container and tube members may vary depending on the amount of sample desired and the applications in which the sampling system will be utilized. For example, conventional ⅛ inch diameter instrumentation tubing and 40 milliliter sample containers can be used.

Figure 3:
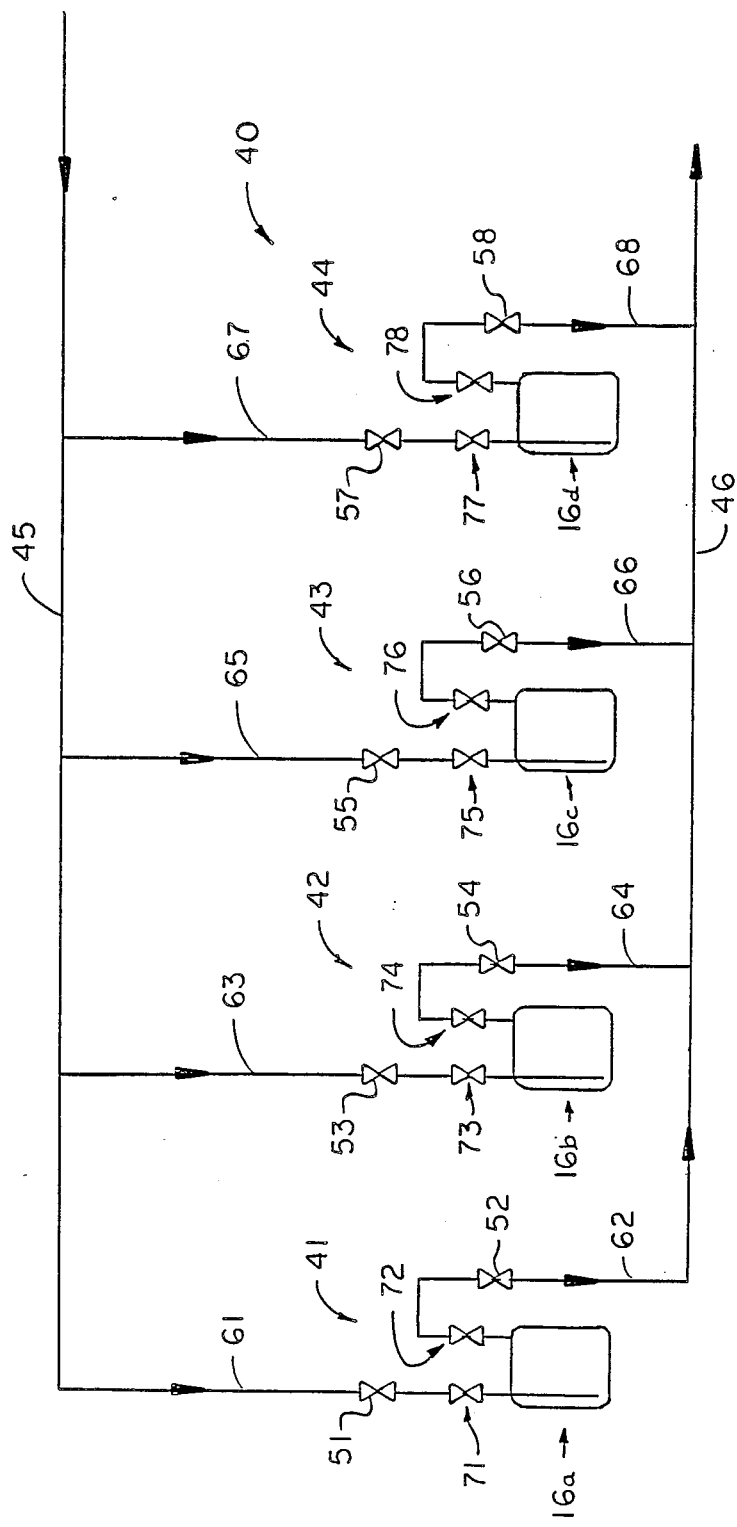
FIG. 3 is a schematic view of another embodiment of the present invention showing a system comprising multiple sample containers of the present invention.

Any number of sample systems described with reference to FIG. 1 can be connected in series or in parallel to obtain multiple samples. With reference to FIG. 3, there is shown one embodiment of the present invention wherein multiple samples can be collected in sequence over a predetermined period of time. In FIG. 3 there is shown four individual sample systems with a common sample inlet and sample outlet. While the preferred embodiment, in this instance, contains four individual sample systems, the present invention is not limited to that number. Any number of individual sample systems can be used. The sampling system shown in FIG. 3 will be referred to herein as "the sampler" and indicated generally as numeral 40.

The sampler 40 shown in FIG. 3 consists of four individual sample systems, indicated generally as numerals 41-44, with a common sample inlet 45 and a common sample outlet 46. Each of the four sample systems utilizes two normally closed, two-way solenoid valves 51-58 and a specially designed sample container 16a-d which is identical to sample container 16 as described with reference to FIG. 2 above. There is one solenoid valve 51, 53, 55 and 57 on the sample inlet 61, 63, 65, 67, respectively, of each sample 15 container 16a-d and one solenoid valve 52, 54, 56 and 58 on the sample outlet 62, 64, 66 and 68, respectively, of each sample container 16a-d. Quick-connect type valves 71-78 of the type described above, are shown in lines 61-68 for removing any of the sample containers 16a-16d from the sampler 40.

A controller (not shown) activates one of the sample systems 41, 42, 43 or 44 by energizing the appropriate set of solenoid valves to allow fluid flow into the corresponding sample container 16a, 16b, 16c or 16d. The sample fluid fills the container and overflows out the outlet tube. The sample container design allows it to be completely filled eliminating all headspace in the container. The sampler's controller deactivates the solenoid valves after a designated time period which blocks in the sample container, therefore preventing evaporation of the sample.

As an illustration of one embodiment of the present invention, the sampler's controller is programmed for a twenty-four hour sampling interval containing four evenly spaced sampling cycles: one cycle every six hours. The first cycle occurs at six hours into the sampling interval and fills sample container 16a, the second cycle occurs at twelve hours and fills sample container 16b, the third cycle occurs at eighteen hours and fills sample container 16c, and the fourth cycle occurs at twenty-four and fills sample container 16d. It is understood that any desired number of cycles and any desired period of time for each cycle can be used.

If the sampler 40 is not in a sampling cycle, all the solenoid valves are closed which blocks in the sample containers and allows no sample flow from the sample inlet to the sample outlet. When the sampler 40 is activated any of the individual sampling system 41-44 may be actuated and the appropriate solenoid valves opened.

For example, as discussed above a first sampling cycle may begin at six hours and thus, the sampler's controller energizes solenoid valves 51 and 52 which opens the valves 51 and 52. The sample then flows through the sample inlet manifold 45 and enters sample container 16a through solenoid valve 51 and the sample container's inlet tube 61 which extends to the bottom of the container. Sample flow fills the sample container 16a from the bottom first. After the container is full, sample flows up into the cone-shaped cap, shown in FIG. 2 as numeral 26 through the bore 29, and overflows out of the sample container's outlet tube 62, through solenoid valve 52, and out the sample outlet manifold 46.

All headspace in the sample container 16a is eliminated during this filling procedure. The cone-shaped top 26 of the sample container 16a and the flush mounting of the outlet tube 62 in the top eliminates the possibility of air bubbles and/or headspace in the sample container 16a.

The sample continues to overflow in the manner described above until the sampling cycle time interval elapses. The sampler's controller then de-energizes the solenoid valves 51 and 52 which closes the valves 51 and 52 stopping sample flow to sample container 16a and ending the first sampling cycle. The closed valves 51 and 52 also block in the sample container 16a thus preventing any evaporation of the sample collected in container 16a.

Each of the four sampling cycles for sample containers 16a-d in sample systems 41-44 are identical in operation as described above. The difference is that the sampler's controller determines the filling sequence by energizing the appropriate pair of solenoid valves. For example, in the second sampling cycle, solenoid valves 53 and 54 are energized filling sample container 16b.

In carrying out one embodiment of the present invention, a sampling system is used to collect samples of a waste water stream. The sampler automatically collects four samples in individual sample containers at six-hour intervals over a twenty-four hour period eliminating all the headspace in the sample containers. The four samples are then collected by personnel and analyzed for components of interest. Components of interest to be analyzed may include, for example, total purgeable halocarbons (RCl) such as vinyl chloride, carbon tetrachloride, perchlorethylene, ethylenedichloride (EDC) and the like.

EXAMPLE

An automatic sampler of the present invention used in this example was similar to the sampling system shown in FIG. 3 except that quick-connect fittings 19 and 20 were not used. Samples collected automatically using the automatic sampler were compared to samples collected manually by manual grab samples and the comparison data is described in the table below. The samples were analyzed for parts per million (ppm) levels of RCls for the comparison. The RCl content in a sample is an indication of whether or not all of the headspace in a sample container has been eliminated from the sample container. Low concentrations of RCls in the sample container indicates a loss of the volatile RCls due to headspace in the containers or to evaporation The results described in the table below show that the automatic sampler had less loss of RCls overall than the manual grab samples.

A unique feature of the sampler is that it automatically collects these multiple individual samples with no headspace and then keeps them over the twenty-four hour period with no loss from evaporation.

| TIME | COMPARATIVE GRAB SAMPLES (PPM RCl) | AUTOMATIC SAMPLER (PPM RCl) | % DEVIATION[1] |
| --- | --- | --- | --- |
| 12:00 PM | 0.13 | 0.15 | 7.1 |
| 8:30 AM | 0.12 | 0.11* | 4.3 |
| 10:30 AM | 0.12 | 0.13 | 4.0 |
| 12:57 PM | 0.15 | 0.15 | 0.0 |
| 10:30 AM | 0.13 | 0.12* | 6.3 |
| 2:10 PM | 0.16 | 0.20 | 11.1 |
| 8:30 AM | 0.13 | 0.17 | 13.3 |

[1]% Relative Standard Deviation ± 0.01
*These samples were exposed to the atmosphere for a short period of time before analysis.

What is claimed is:

1. A method of collecting samples of fluid in a sampling apparatus having a bottom and a top with zero head space said method comprising activating valve means such that a fluid stream is flowed into the sampling apparatus near the bottom and exits near the top sufficient to purge the head space in the container, said sampling apparatus comprising
   (a) a sample container adapted for holding a fluid with zero head space,
   (b) a removable cap means removably fastened to said sample container, said cap means having an inner and outer surface, said inner surface of said cap means being tapered such that the inner surface of said cap means is generally conical in shape when viewed din cross-section;
   (c) a bore at the apex of said conically shaped cap means for passing fluid therethrough;
   (d) an inlet conduit passing through said cap means and adapted for introducing a stream of fluid into said sample container;
   (e) an outlet conduit passing through said cap means and adapted for removing a stream of fluid from said sample container, said outlet conduit integral with said bore at the apex of said conically shaped cap means;
   (f) a means associated with the cap means for purging to eliminate any air gap or head space within the container comprising a first valve on said inlet conduit for passing a stream therethrough and into the sample container, a second valve on said outlet conduit for passing a stream therethrough and out of the sample container; and
   (g) a controller for actuating the fist and second valves such that a stream of fluid fills the sample container and overflows out of the sample container for a predetermined time interval such that any head space in said container is eliminated.

2. The method of claim 1 carried out automatically.

3. The method of claim 1 wherein the fluid is flowed through the container for a predetermined amount of time.

4. A method of collecting multiple samples of fluid in a series of containers with zero head space comprising:
   (a) actuating at least a first valve means such that a fluid stream is flowed into at least a first sample container;
   (b) flowing fluid through the first sample container for a predetermined time interval;
   (c) actuating the first valve means such that the fluid stream to the first container is stopped after a predetermined time interval;
   (d) actuating a second valve means such that a fluid stream is flowed into a second sample container (e) flowing fluid through second sample container for a predetermined time interval; and (f) actuating the second valve means such that the fluid stream to the second container is stopped after a predetermined time interval, each of said collections ample containers comprising a container with a removable cap means, said cap means having an inner and outer surface, an inlet conduit means passing from cap means outer to inner surface adapted for introducing a fluid into said container and an outlet conduit means passing from cap means inner to outer surface adapted for removing a fluid from the container, said inner surface of said cap means being conical in shape when viewed in cross section, a bore at the top of said cone for passing fluid therethrough, said outlet conduit integral with said borer at the apex of said cone.

* * * * *

UNITED STATES PATENT AND TRADEMARK OFFICE
CERTIFICATE OF CORRECTION

PATENT NO. : 4,974,456

DATED : December 4, 1990

INVENTOR(S) : Patricia Ortiz et al

It is certified that error appears in the above-identified patent and that said Letters Patent is hereby corrected as shown below:

Col. 1, line 25, shown as; "at volume" should read --a volume--.
Col. 1, line 27, shown as; "(every/six hours): should read --every six hours--.
Col. 4, line 24, shown as; "sample 15 container" should read --sample container--.
Col. 4, line 34, shown as; "cycles:" should read --cycles;--.
Col. 5, line 56, shown as; "evaporation The" should read --evaporation. The--.
Col. 6, line 30, shown as; "viewed din" should read --viewed in--.
Col. 6, line 48, shown as; the fist" should read --the first--.
Col. 8, line 7, shown as; "borer" should read --bore--.

Signed and Sealed this

Fourteenth Day of July, 1992

Attest:

DOUGLAS B. COMER

*Attesting Officer*   *Acting Commissioner of Patents and Trademarks*